United States Patent
Lihl et al.

(10) Patent No.: US 10,073,016 B2
(45) Date of Patent: Sep. 11, 2018

(54) FREEZE FRACTURE MACHINE

(71) Applicant: Leica Mikrosysteme GmbH, Vienna (AT)

(72) Inventors: Reinhard Lihl, Vienna (AT); Michael Zimmermann, Leopoldsdorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 110 days.

(21) Appl. No.: 14/953,313

(22) Filed: Nov. 28, 2015

(65) Prior Publication Data

US 2016/0178487 A1    Jun. 23, 2016

(30) Foreign Application Priority Data

Dec. 17, 2014  (DE) .......................... 10 2014 118 801

(51) Int. Cl.
*G01N 1/28* (2006.01)
*G01N 1/42* (2006.01)

(52) U.S. Cl.
CPC .............. *G01N 1/286* (2013.01); *G01N 1/42* (2013.01); *G01N 2001/2873* (2013.01)

(58) Field of Classification Search
CPC .. G01N 1/286; G01N 1/42; G01N 2001/2873; H01J 37/20
See application file for complete search history.

(56) References Cited

U.S. PATENT DOCUMENTS

| 3,699,830 A | * | 10/1972 | Pickett | A61B 17/322 83/13 |
| 4,284,894 A | * | 8/1981 | Sitte | A61B 10/00 250/443.1 |
| 5,043,144 A | * | 8/1991 | Gordon | B01L 9/50 250/440.11 |

(Continued)

FOREIGN PATENT DOCUMENTS

| GB | 1245411 | 9/1971 |
| JP | S53031485 | 3/1978 |

(Continued)

OTHER PUBLICATIONS

Leica Mikrosysteme GMBH, Leica EM VCT100 Vacuum Cryo Transfer (Product Brochure), May 2009, Vienna, Austria.

*Primary Examiner* — Jonathan Riley
(74) *Attorney, Agent, or Firm* — Hodgson Russ LLP (57) ABSTRACT

A freeze fracture machine (100) comprises a vacuum chamber (110); a sample receptacle (160) for receiving a sample to be processed and a knife receptacle (150) for receiving a knife (110) for processing of the sample arranged in the vacuum chamber (155); a transfer lock (130) on the vacuum chamber (110) through which a sample and a knife (155) are introducible into the vacuum chamber (155) and positionable in the vacuum chamber (110) by means of a positioning apparatus (135); the sample and the sample receptacle (160) being positionable with respect to one another such that the sample is mountable on the sample receptacle (160) by means of the positioning apparatus (135); and the knife (Continued)

(155) and the knife receptacle (150) being positionable with respect to one another such that the knife (155) is mountable on the knife receptacle (150) by means of the positioning apparatus (135).

12 Claims, 5 Drawing Sheets

(56) References Cited

U.S. PATENT DOCUMENTS

| | | | | |
|---|---|---|---|---|
| 5,092,210 A * | 3/1992 | Dern | ............ | B26D 3/28 |
| | | | | 30/49 |
| 5,299,481 A * | 4/1994 | Lihl | ............ | F25D 3/10 |
| | | | | 62/320 |
| 5,352,898 A * | 10/1994 | Mehta | ............ | G01N 1/286 |
| | | | | 250/304 |
| 5,461,953 A * | 10/1995 | McCormick | ............ | G01N 1/06 |
| | | | | 83/36 |
| 7,596,957 B2 * | 10/2009 | Fuhr | ............ | B25J 21/02 |
| | | | | 62/78 |
| 2008/0202308 A1 * | 8/2008 | Fujiwara | ............ | G01N 1/06 |
| | | | | 83/703 |
| 2009/0078060 A1 * | 3/2009 | Moore | ............ | B25J 21/02 |
| | | | | 73/863 |
| 2011/0027876 A1 * | 2/2011 | Lihl | ............ | G01N 1/42 |
| | | | | 435/307.1 |
| 2013/0319328 A1 | 12/2013 | Wurzinger et al. | | |
| 2014/0033888 A1 | 2/2014 | Walter | | |
| 2014/0041500 A1 | 2/2014 | Isagawa et al. | | |
| 2015/0268134 A1 | 9/2015 | Miyatani | | |

FOREIGN PATENT DOCUMENTS

| | | |
|---|---|---|
| JP | H03208245 | 9/1991 |
| JP | H10115624 | 5/1998 |
| WO | 01/84110 A2 | 11/2001 |

* cited by examiner

FREEZE FRACTURE MACHINE

CROSS REFERENCE TO RELATED APPLICATIONS

This application claims priority of German patent application number 10 2014 118 801.2 filed Dec. 17, 2014, the entire disclosure of which is incorporated by reference herein.

FIELD OF THE INVENTION

The present invention relates to a freeze fracture machine having a vacuum chamber, and to a method for introducing a sample and a knife into a vacuum chamber of a freeze fracture machine of this kind.

BACKGROUND OF THE INVENTION

Freeze fracture machines serve for the processing of frozen samples such as tissue samples. The frozen sample can be sectioned or fractured, by means of a knife, in a vacuum chamber of the freeze fracture machine. The vacuum chamber or vacuum serves in particular to eliminate water that could contaminate the sample. In addition, both the sample and the knife are cooled, usually with liquid nitrogen, so that the frozen sample does not become heated during processing.

A viewing window, through which the sample to be processed is visible, is usually provided in the freeze fracture machine or in the vacuum chamber thereof. A microscope can furthermore be provided, for example, if very small samples are to be processed.

A transfer lock, through which the sample can be introduced into or removed from the vacuum chamber without interrupting the vacuum, can be provided on the freeze fracture machine for the introduction and removal of a sample.

In order to introduce or remove a knife, for example in order to change a knife type or replace a contaminated knife, it has hitherto been necessary to break the vacuum, aerate the vacuum chamber, and change the knife via the viewing window or a corresponding door. It is disadvantageous here that as a result of the aeration and re-evacuation, the knife changing procedure takes a very long time. In addition, the entire vacuum chamber must be heated to room temperature so that the knife can be changed.

It is therefore desirable to describe a capability for faster and simpler changing of a knife and a sample in the context of a freeze fracture machine.

SUMMARY OF THE INVENTION

A freeze fracture machine and a method for introducing a sample and a knife into a vacuum chamber of a freeze fracture machine are proposed according to the present invention.

A freeze fracture machine of the present invention generally comprises a vacuum chamber; a sample receptacle for receiving a sample to be processed, the sample receptacle being arranged in the vacuum chamber; a knife receptacle for receiving a knife provided for processing of the sample, the knife receptacle being arranged in the vacuum chamber; a transfer lock through which the sample and the knife are introducible into the vacuum chamber; and a positioning apparatus provided on the vacuum chamber, the positioning apparatus being operable to introduce the sample and the knife into the vacuum chamber through the transfer lock and position the sample and the knife in the vacuum chamber. The sample and the sample receptacle are positionable with respect to one another such that the sample is mountable on the sample receptacle by operation of the positioning apparatus. The knife and the knife receptacle are positionable with respect to one another such that the knife is mountable on the knife receptacle by operation of the positioning apparatus.

A method for introducing a sample and a knife into a vacuum chamber of a freeze fracture machine according to the present invention generally comprises the steps of introducing the sample via the transfer lock into the vacuum chamber and mounting the sample on the sample receptacle by operating the positioning apparatus; and introducing the knife via the transfer lock into the vacuum chamber and mounting the knife on the knife receptacle by operating the positioning apparatus.

Advantageous embodiments are the subject matter of the description that follows.

ADVANTAGES OF THE INVENTION

A freeze fracture machine according to the present invention comprises a vacuum chamber; a sample receptacle for receiving a sample to be processed, and a knife receptacle for receiving a knife provided for processing of the sample, are arranged in the vacuum chamber. Provided on the vacuum chamber is a transfer lock through which a sample and a knife are introducible into the vacuum chamber and positionable in the vacuum chamber by means of a positioning apparatus.

The sample and the sample receptacle are positionable with respect to one another in such a way that the sample is mountable on the sample receptacle by means of the positioning apparatus, and the knife and the knife receptacle are positionable with respect to one another in such a way that the knife is mountable on the knife receptacle by means of the positioning apparatus.

A freeze fracture machine of this kind thus makes it possible to change both a sample and a knife through one and the same transfer lock. This has the advantage that the vacuum chamber does not need to be aerated and heated either in order to change the sample or in order to change the knife. A sample change and also, in particular, a knife change can thus be carried out in very quick and uncomplicated fashion.

A "transfer lock" is understood as an opening in the vacuum chamber which is closable with a vacuum-tight door (usually embodied as a slide valve). A vacuum transfer system (ideally a vacuum cryo transfer system) can then be flange-mounted onto such a transfer lock. Once the vacuum transfer system is evacuated, the door can be opened with no pressure loss or temperature increase in the vacuum chamber. The positioning apparatus can, in particular, be part of a vacuum transfer system of this kind. A preferred vacuum cryo transfer system is offered by the Applicant, for example, under the designation EM VCT100.

Preferably the knife receptacle is bringable into a changing position, and in the changing position the knife is mountable on the knife receptacle. For this purpose the knife receptacle can be displaceable, for example, along a rail or the like. Further displacement mechanisms, by means of which the knife receptacle is displaceable in various directions, can likewise be provided. The knife receptacle can thus be brought into a maximally favorable position relative to the transfer lock. In this manner, for example, a transfer lock that has hitherto been used to to change the sample can thus very easily also be used to change the knife. A working position in which the knife assumes a desired position for sectioning the sample can be provided, for example, as a further position. Multiple working positions are also conceivable.

Advantageously, a knife holder for immobilizing the knife is mountable on the positioning apparatus, and the knife holder is connectable to the knife receptacle.

This makes possible particularly simple introduction of a knife into the vacuum chamber, since a knife holder can be mounted in particularly simple fashion on the positioning apparatus, which can be e.g. a slide rod, for example by simply being placed on.

It is advantageous if a sample holder for immobilizing the sample is mountable on the positioning apparatus, the sample holder being connectable to the sample receptacle. This makes possible particularly simple introduction of a sample into the vacuum chamber, since a sample holder, like the knife holder, is mountable on the positioning apparatus in particularly simple fashion.

Preferably the knife receptacle comprises receiving means for establishing a connection of the knife holder to the knife receptacle. This makes possible simple and stable mounting of the knife holder. For example, the receiving means can be two spaced-apart rails into which the knife holder can be inserted.

Advantageously, the sample receptacle comprises receiving means for establishing a connection of the sample holder to the sample receptacle, the receiving means of the knife holder and of the sample holder in particular being configured similarly. This on the one hand makes possible simple and stable mounting of the sample holder, as in the case of the knife receptacle. In addition, if the two receiving means are configured similarly, similar holders can be used as sample holders and as knife holders.

It is advantageous if the knife holder comprises fastening means, corresponding to the receiving means of the knife receptacle, which are actuatable by means of the positioning apparatus in order to establish the connection of the knife holder to the knife receptacle. Such fastening means can be, for example, bolts impinged upon by spring force. These bolts can then be retracted, for example, by rotating the positioning apparatus, in particular when it is a slide rod. After introduction into the receiving means of the knife receptacle, these bolts can then be nonpositively and/or positively connected to the receiving means.

Preferably the sample holder comprises fastening means, corresponding to the receiving means of the sample receptacle, which are actuatable by means of the positioning apparatus in order to establish the connection of the sample holder to the sample receptacle, the fastening means of the knife holder and of the sample holder in particular being configured similarly. The result is that, as in the case of the knife holder, a simple and secure connection can be established between the sample receptacle and the sample holder. In particular, similar holders can thus be used as sample holders and knife holders, such that a sample can be mounted on one holder and a knife on the other holder.

Advantageously, the sample receptacle is arranged at a fixed position in the vacuum chamber. Particularly simple mounting of the sample on the sample receptacle can thereby be enabled. This furthermore ensures that the sample receptacle is always located in the same position, so that accurately placed processing actions are possible.

It is advantageous if the positioning apparatus is configured to displace the sample or the knife inside the vacuum chamber along an axis. This makes possible a simple configuration of the positioning apparatus, for example in the form of a slide rod. Simple changing of the knife is thereby enabled, especially in combination with the displaceable knife receptacle. Advantageously, the positioning apparatus comprises a magnetically coupled rotary/slide lead-through for vacuum. This can also be a bellows-sealed or elastomer-sealed rotary/slide lead-through.

Preferably the sample receptacle and/or the knife receptacle comprise a connector for a coolant. The coolant can be, in particular, liquid nitrogen. The sample receptacle or knife receptacle can comprise, for example, a copper block by way of which a coolant line can be connected and through which the coolant is directed.

Continuous cooling of the sample during processing is thereby ensured.

A method according to the present invention serves for introduction of a sample and of a knife into a vacuum chamber of a freeze fracture machine according to the present invention. At a first point in time the sample is introduced via the transfer lock into the vacuum chamber and mounted on the sample receptacle by means of the positioning apparatus; and at a second point in time the knife is introduced via the transfer lock into the vacuum chamber and mounted on the knife receptacle by means of the positioning apparatus.

It is thus possible thereby to change both a sample and a knife through only one transfer lock. This has the advantage that the vacuum chamber does not need to be aerated and heated either in order to change the sample or in order to change the knife. A sample change, and in particular also a knife change, can thus be carried out in very quick and uncomplicated fashion.

Further advantages and embodiments of the invention are evident from the description and the appended drawings.

It is understood that the features recited above and those yet to be explained below are usable not only in the respective combination indicated, but also in other combinations or in isolation, without departing from the scope of the present invention.

BRIEF DESCRIPTION OF THE DRAWING VIEWS

The invention is depicted schematically in the drawings on the basis of an exemplifying embodiment, and will be described below with reference to the drawings.

DETAILED DESCRIPTION OF THE INVENTION

Figure 1:
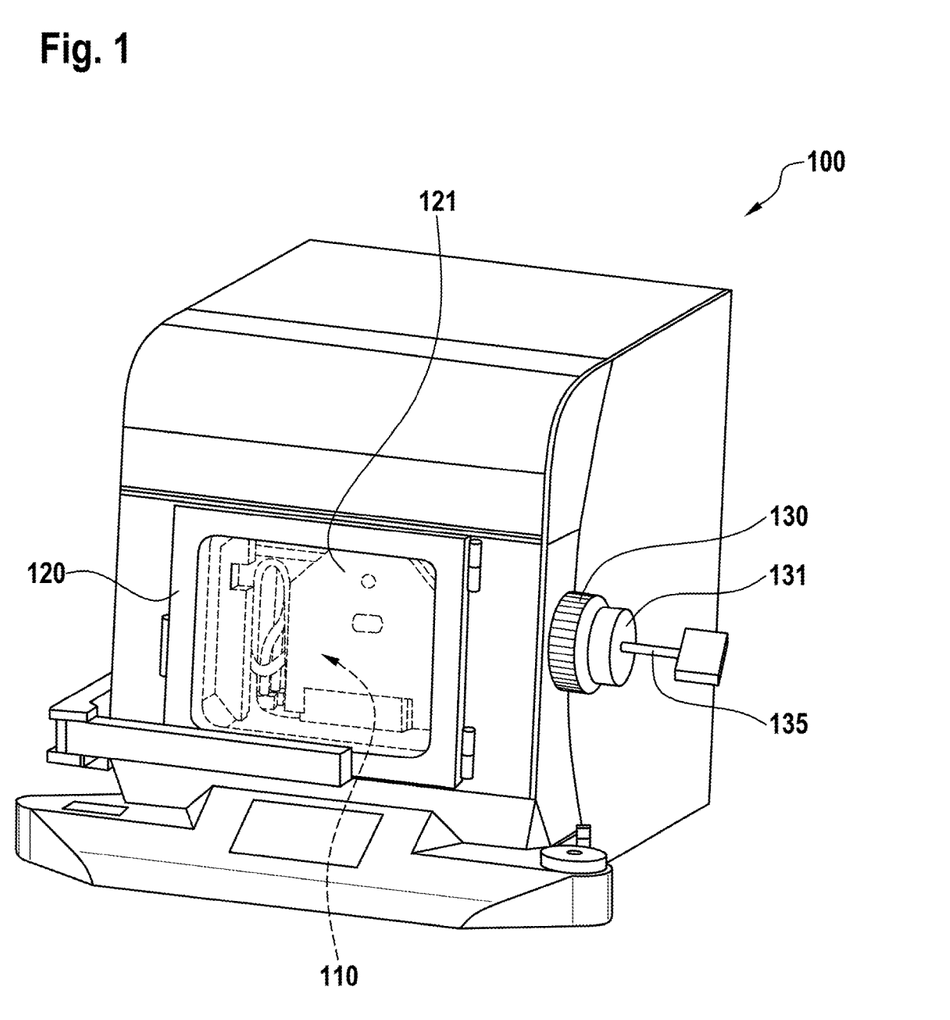
FIG. 1 schematically shows a freeze fracture machine according to the present invention in a preferred embodiment.

FIG. 1 schematically depicts a freeze fracture machine 100 according to the present invention in a preferred embodiment. A door 120 having a viewing window 121 is provided on the front side. Through door 120, access is enabled to vacuum chamber 110, which is located in the interior of the freeze fracture machine or is constituted by its interior. Viewing window 121, which is made e.g. of glass that is introduced into door 120, allows observation of operations in vacuum chamber 110.

A transfer lock 130, which enables access to vacuum chamber 110, is provided on the side of freeze fracture machine 100. A valve by which vacuum chamber 110 can be closed off from the outside in airtight fashion is provided, for example, in transfer lock 130. A housing 131 can be mounted on transfer lock 130 in airtight fashion, for example by means of a bayonet closure. A positioning apparatus embodied as a slide rod 135 is provided in housing 131. This slide rod 135 is arranged in housing 131 in airtight fashion, for example by means of a seal, in such a way that it is displaceable along its axis relative to housing 131 and is rotatable. It is part of an elastomer-sealed rotary/slide leadthrough.

Once housing 131 has been mounted on transfer lock 130 in airtight fashion, and while the transfer lock, in particular the valve thereof, is still closed, the interior of housing 131 as far as the valve is pumped out, for example by means of a vacuum pump. Once a sufficiently good vacuum is achieved, the valve or transfer lock 130 is opened to vacuum chamber 110.

By means of slide rod 135, both a sample (previously mounted thereon) and a knife can be introduced through the transfer lock into vacuum chamber 110, and likewise removed again from vacuum chamber 110.

Figure 2:
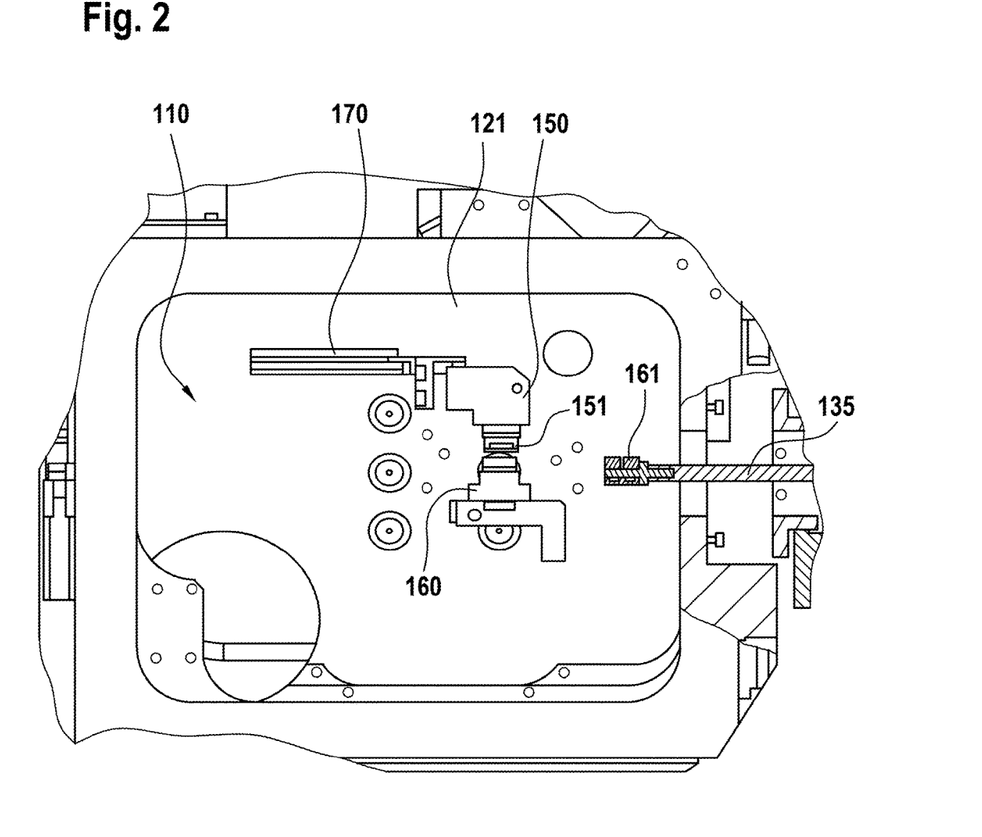
FIG. 2 schematically shows a portion of the freeze fracture machine of FIG. 1.

FIG. 2 schematically shows a portion of freeze fracture machine 100, in particular an interior view of vacuum chamber 110. A knife receptacle 150, which comprises, for example, a copper block cooled with liquid nitrogen, is provided in vacuum chamber 110. Knife receptacle 150 is displaceable via a rail 170 between a working position and a changing position.

Also provided is a sample receptacle 160 that is arranged at a fixed position in vacuum chamber 110. Like knife receptacle 150, sample receptacle 160 comprises a copper block through which liquid nitrogen flows. A cooling system for supplying knife receptacle 150 and sample receptacle 160 with liquid nitrogen is not depicted in the interest of clarity.

Knife receptacle 150 and sample receptacle 160 are displaceable relative to one another in order to section or break a sample.

Visible on the right side is slide rod 135 with its vacuum-chamber-side end on which, for example, a sample holder 161 is mounted. Sample receptacle 160 and slide rod 135 are positioned or arranged with respect to one another in such a way that sample holder 161 can be mounted on sample receptacle 160 by moving slide rod 135 along its axis.

Figure 3:
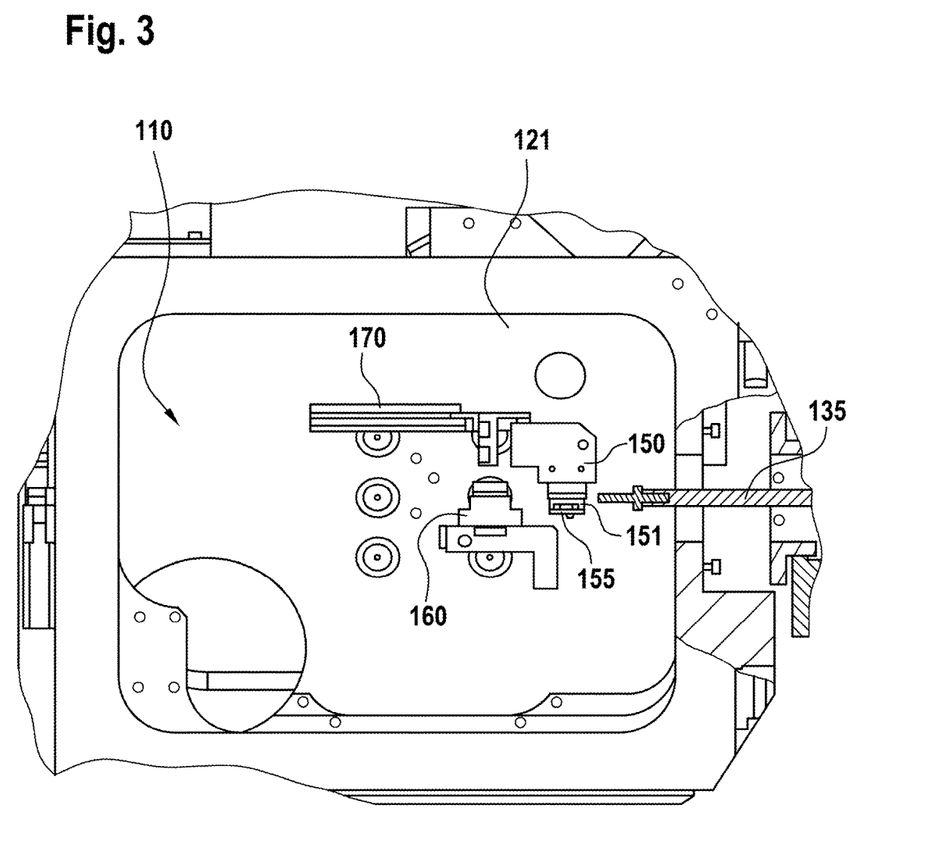
FIG. 3 schematically shows the portion of the freeze fracture machine of FIG. 2 in a different working position.

FIG. 3 shows the portion of freeze fracture machine 100 of FIG. 2, with knife receptacle 150 in the changing position. For this, knife receptacle 150 is displaced horizontally and vertically along rail 150. The movement of knife receptacle 150 into the changing position (and also correspondingly back into the working position) is accomplished preferably automatically by means of a corresponding control system and drives. Manual displacement is likewise conceivable, however, for example via a lever.

When knife receptacle 150 is in the changing position, knife receptacle 150 and slide rod 135 are positioned or arranged with respect to one another in such a way that a knife holder mounted at the end of the axis can be mounted on knife receptacle 150 by moving slide rod 135 along its axis.

Figure 4:
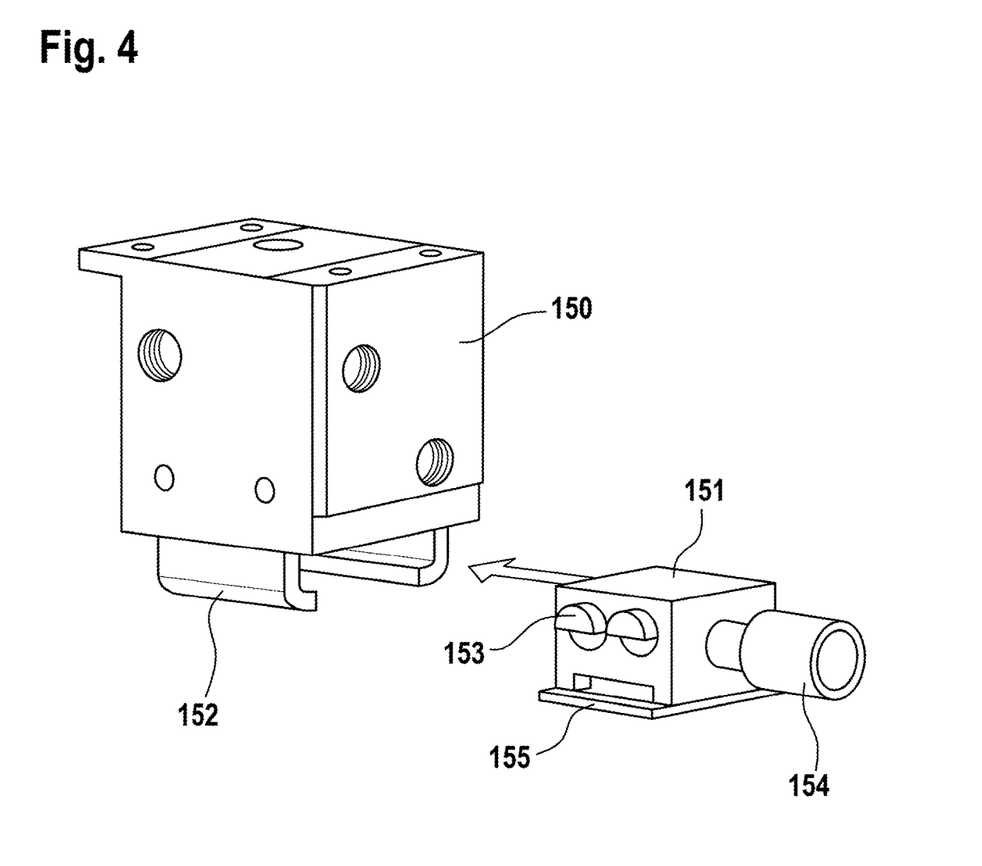
FIG. 4 schematically shows a knife receptacle and a knife holder for a freeze fracture machine according to the present invention.

FIG. 4 depicts, schematically and by way of example, a knife receptacle 150 and a knife holder 151 for freeze fracture machine 100. Knife receptacle 150 here is in the changing position shown in FIG. 3. Introduced into knife holder 151 is a holding apparatus 154 that can be mounted, for example, at one end of slide rod 135.

Knife holder 151 comprises fastening means 153 that are embodied in the present case as bolts impinged upon by a spring force. A knife 155 is furthermore mounted on the underside of knife holder 151, for example by means of a screw connection or clamp connection. Knife holder 151 is embodied in such a way that different knife shapes and knife materials can be mounted thereon.

Knife receiver 150 comprises receiving means 152, in the present case in the form of two rails, on its underside. Knife holder 151 can be mounted by means of slide rod 135 on knife receptacle 150, by sliding knife holder 151 into receiving means 152. By means of slide rod 135, or holding apparatus 154 mounted thereon, the bolts can be retracted against the spring force so that knife holder 151 can easily be slid into the receiving means. A rotary mechanism, for example, in which slide rod 135 is rotated and the bolts are thereby retracted, can be provided for this purpose.

As soon as the knife holder is located in its target position in the receiving means, the bolts can be released again. Depending on the exact embodiment of receiving means 152, a positive and/or nonpositive connection can thereby be established.

Figure 5:
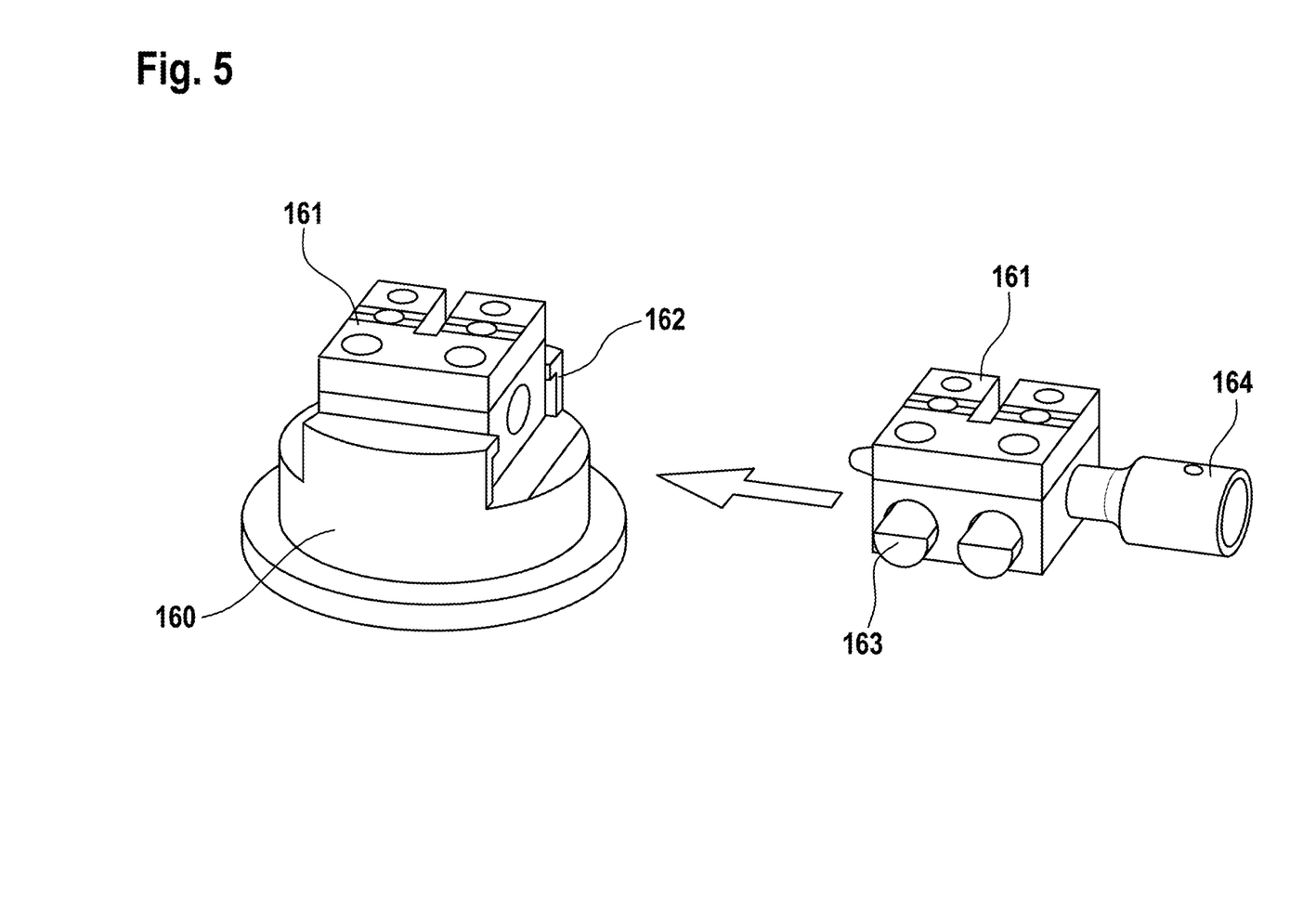
FIG. 5 schematically shows a sample receptacle and a sample holder for a freeze fracture machine according to the present invention.

FIG. 5 depicts, schematically and by way of example, a sample receptacle 160 and a sample holder 161 for freeze fracture apparatus 100. Sample receptacle 160 here is located in the position shown in FIG. 2 or FIG. 3. Introduced into sample holder 161 is a holding apparatus 164 that can be mounted, for example, at one end of slide rod 135.

Sample holder 161 comprises fastening means 163 that in the present case are embodied, like fastening means 153 of knife holder 151, as bolts impinged upon by a spring force. A sample can be mounted on the upper side of sample holder 161, for example by means of a screw connection, clamp connection, or adhesive connection.

Sample receptacle 160 comprises receiving means 162, in the present case in the form of two rails, on its upper side. Sample holder 161 can be mounted by means of slide rod 135 on sample receptacle 160, by sliding sample holder 161 into receiving means 162. A sample holder 161 introduced into sample receptacle 160 is depicted by way of example in FIG. 5.

The introduction of sample holder 161 into receiving means 162 of sample receptacle 160 is accomplished in the same manner as with knife holder 151 and receiving means 152 of knife receptacle 150. In particular, fastening means 163 are embodied similarly to fastening means 153. Holding apparatus 164 is likewise configured similarly to holding apparatus 154.

The mounting of knife holder 151 and of sample holder 161 thus functions according to the same principle. The only differences are the displacement of the knife receptacle, and knife holder 151 that is to be introduced with a 180° rotation with respect to sample holder 161.

Removal of the knife holder and of the sample holder proceeds in reverse order as compared with introduction. The knife holder or sample holder, optionally in a changing position that is to be established, is released from the relevant receptacle with slide rod 135, accompanied by actuation of the fastening means, and removed via transfer lock 130.

What is claimed is:

1. A freeze fracture machine (100) comprising:
a vacuum chamber (110);
a sample receptacle (160) for receiving a sample to be processed, the sample receptacle (160) being arranged in the vacuum chamber (110);
a knife receptacle (150) for receiving a knife (155) provided for processing of the sample, the knife receptacle (150) being arranged in the vacuum chamber (110);
a transfer lock (130) through which the sample and the knife (155) are introducible into the vacuum chamber (110);
a positioning apparatus (135) provided on the vacuum chamber (110), the positioning apparatus (135) being operable to introduce the sample and the knife (155) into the vacuum chamber (110) through the transfer lock (130) and position the sample and the knife (155) in the vacuum chamber (110);
the sample being positionable with respect to the sample receptacle (160) by operation of the positioning apparatus (135) such that the sample is mountable on the sample receptacle (160) by operation of the positioning apparatus (135);
the knife (155) being positionable with respect to the knife receptacle (150) by operation of the positioning apparatus (135) such that the knife (155) is mountable on the knife receptacle (150) by operation of the positioning apparatus (135); and
a knife holder (151) for immobilizing the knife (155), wherein the knife holder (151) is mountable on the positioning apparatus (135) and is connectable to the knife receptacle (150);
wherein the positioning apparatus (135) includes a slide rod removably mountable on the transfer lock (130), and the knife holder (151) is mountable at an end of the slide rod and is transferable from the end of the slide rod to the knife receptacle (150) by moving the slide rod relative to the knife receptacle (150).

2. The freeze fracture machine (100) according to claim 1, wherein the knife receptacle (150) is positionable into a changing position, and the positioning apparatus (135) is operable to mount the knife (155) on the knife receptacle (150) when the knife receptacle (150) is at the changing position.

3. The freeze fracture machine (100) according to claim 1, further comprising a sample holder (161) for immobilizing the sample, wherein the sample holder (161) is mountable on the positioning apparatus (135) and is connectable to the sample receptacle (160).

4. The freeze fracture machine (100) according to claim 3, wherein the knife receptacle (150) comprises receiving means (152) for receiving the knife holder (151) to establish a connection of the knife holder (151) to the knife receptacle (150).

5. The freeze fracture machine (100) according to claim 4, wherein the sample receptacle (160) comprises receiving means (162) for receiving the sample holder (161) to establish a connection of the sample holder (161) to the sample receptacle (160).

6. The freeze fracture machine (100) according to claim 4, wherein the receiving means (152) for receiving the knife holder (151) and the receiving means (162) for receiving the sample holder (161) each include two spaced apart rails.

7. The freeze fracture machine (100) according to claim 5, wherein the knife holder (151) comprises fastening means (153) corresponding to the receiving means (152) of the knife receptacle (150), wherein the fastening means (153) of the knife holder (151) are actuatable by operation of the positioning apparatus (135) to establish the connection of the knife holder (151) to the knife receptacle (150).

8. The freeze fracture machine (100) according to claim 7, wherein the sample holder (161) comprises fastening means (163) corresponding to the receiving means (162) of the sample receptacle (160), wherein the fastening means (163) of the sample holder (161) are actuatable by operation of the positioning apparatus (135) to establish the connection of the sample holder (161) to the sample receptacle (160).

9. The freeze fracture machine (100) according to claim 8, wherein the fastening means (153) of the knife holder (151) and the fastening means (163) of the sample holder (161) each include bolts.

10. The freeze fracture machine (100) according to claim 1, wherein the sample receptacle (160) is arranged at a fixed position in the vacuum chamber (110).

11. The freeze fracture machine (100) according to claim 1, wherein the positioning apparatus (135) is configured to displace the sample or the knife (155) inside the vacuum chamber (110) along an axis.

12. The freeze fracture machine (100) according to claim 1, wherein the slide rod is removably mountable on the transfer lock (130) by way of a housing (131) in which the slide rod is provided.

* * * * *